(12) United States Patent
Serrano

(10) Patent No.: US 11,439,604 B1
(45) Date of Patent: Sep. 13, 2022

(54) PLANT PHENOLS EXTRACTION AND ACTIVATION THEREOF, TO USE AS FEED ADDITIVE IN ANIMAL HUSBANDRY PARTICULARLY RUMINANTS TO HELP REDUCING CO2 FROM ENVIRONMENT

(71) Applicant: Manuel Serrano, Madera, CA (US)

(72) Inventor: Manuel Serrano, Madera, CA (US)

(*) Notice: Subject to any disclaimer, the term of this patent is extended or adjusted under 35 U.S.C. 154(b) by 0 days.

(21) Appl. No.: 17/466,644

(22) Filed: Sep. 3, 2021

Related U.S. Application Data

(60) Provisional application No. 63/155,889, filed on Mar. 3, 2021.

(51) Int. Cl.
| | | |
|---|---|---|
| *A61K 31/05* | (2006.01) | |
| *A23K 10/14* | (2016.01) | |
| *A23K 20/105* | (2016.01) | |
| *A23K 20/111* | (2016.01) | |
| *A23K 20/174* | (2016.01) | |
| *A23K 20/179* | (2016.01) | |
| *A23K 50/10* | (2016.01) | |
| *A61K 9/00* | (2006.01) | |
| *A61K 47/44* | (2017.01) | |
| *C12P 7/22* | (2006.01) | |

(52) U.S. Cl.
CPC .............. *A61K 31/05* (2013.01); *A23K 10/14* (2016.05); *A23K 20/105* (2016.05); *A23K 20/111* (2016.05); *A23K 20/174* (2016.05); *A23K 20/179* (2016.05); *A23K 50/10* (2016.05); *A61K 9/0056* (2013.01); *A61K 47/44* (2013.01); *C12P 7/22* (2013.01)

(58) Field of Classification Search
CPC ...... A61K 31/05; A61K 47/44; A61K 9/0056; A23K 10/14; A23K 20/105; A23K 20/111; A23K 20/174; A23K 20/179; A23K 50/10; C12P 7/22
See application file for complete search history.

(56) References Cited

U.S. PATENT DOCUMENTS

2013/0280409 A1* 10/2013 Mushock ............... A23L 27/70
426/651

* cited by examiner

*Primary Examiner* — Trevor Love
(74) *Attorney, Agent, or Firm* — Tue Nguyen

(57) ABSTRACT

Feed additive including sodium carbonate feed additive polyphenol particles can be fed to animals to reduce methane or carbon dioxide emission. The feed additive polyphenol particles can be prepared by reacting phenols with sodium percarbonate ($2Na_2CO_3 \cdot 3H_2O_2$) in a solution of water, a peroxidase and a dispersing agent. The sodium percarbonate can be dissolved in the water solution to generate sodium and carbonate ions, which can be incorporated to the polyphenol particles for assisting the animals in digesting the feed additive. The dispersing agent can be used to limit the sizes of the particles to facilitate the consumption of the feed additive by the animals.

6 Claims, 3 Drawing Sheets

---

Preparing a solution comprising a phenolic compound, an oxidizing agent, an enzyme and a dispersing agent, wherein the phenolic compound, the oxidizing agent, and the enzyme are configured to generate an enzyme catalyzed oxidative polymerization of the phenolic compound, wherein the dispersing agent is configured to limit a coalescent of polymer products formed by the enzyme catalyzed oxidative polymerization of the phenolic compound to achieve predetermined sizes
100

Removing the polymer products from the solution to be used as a feed additive for an animal to reduce methane or carbon dioxide emission
110

---

Preparing a solution comprising a phenolic compound, an oxidizing agent comprising sodium percarbonate, an enzyme comprising horseradish peroxidase, and a dispersing agent comprising a plant or seed oil, wherein the phenolic compound, the oxidizing agent, and the enzyme are configured to generate an enzyme catalyzed oxidative polymerization of the phenolic compound to form sodium carbonate phenolic particles, wherein the dispersing agent is configured to limit a coalescent of phenolic particles to achieve predetermined sizes
130

Removing the phenolic particles from the solution to be used as a feed additive for an animal to reduce methane or carbon dioxide emission
140

Preparing a solution comprising a phenolic compound, an oxidizing agent, an enzyme and a dispersing agent, wherein the phenolic compound, the oxidizing agent, and the enzyme are configured to generate an enzyme catalyzed oxidative polymerization of the phenolic compound, wherein the dispersing agent is configured to limit a coalescent of polymer products formed by the enzyme catalyzed oxidative polymerization of the phenolic compound to achieve predetermined sizes
100

Removing the polymer products from the solution to be used as a feed additive for an animal to reduce methane or carbon dioxide emission
110

*FIG. 1A*

Preparing a solution comprising a phenolic compound, an oxidizing agent comprising sodium percarbonate, an enzyme comprising horseradish peroxidase, and a dispersing agent comprising a plant or seed oil,
wherein the phenolic compound, the oxidizing agent, and the enzyme are configured to generate an enzyme catalyzed oxidative polymerization of the phenolic compound to form sodium carbonate phenolic particles,
wherein the dispersing agent is configured to limit a coalescent of phenolic particles to achieve predetermined sizes
130

Removing the phenolic particles from the solution to be used as a feed additive for an animal to reduce methane or carbon dioxide emission
140

PLANT PHENOLS EXTRACTION AND ACTIVATION THEREOF, TO USE AS FEED ADDITIVE IN ANIMAL HUSBANDRY PARTICULARLY RUMINANTS TO HELP REDUCING CO2 FROM ENVIRONMENT

The present patent application claims priority from U.S. Provisional Patent Application Ser. No. 63/155,889, filing date Mar. 3, 2021, entitled "Plant phenols extraction and activation thereof, to use as feed additive in animal husbandry particularly ruminants to help eliminate CO2 from environment", hereby incorporated by reference in its entirety.

The present invention relates to the reduction of methane and carbon dioxide emissions from animals, especially ruminants, through orally administering feed additives mixed in the animal feed.

BACKGROUND OF THE INVENTION

Livestock emissions can include $CH_4$ and $CO_2$, which contribute a large portion of greenhouse gases, which also include water vapor, nitrous oxide, and ozone. The greenhouse gases partially absorb the infra-red radiation emitted by the earth surface, which hampers its dissipation to the space. An increase in the greenhouse gases can result in the raise of global mean temperature.

Methane is a by-product of the consumption of nutrients by microbes in the gut of ruminant animals. For example, a cow releases between 85 and 170 kg of methane per year on average. The rumen, e.g., a first stomach of a ruminant animal, is filled with microorganisms, such as bacteria, fungi and protozoa that break down high fiber plant material consume by the animal into nutrients via a fermentative process. The microorganisms process the plant material to produce methane and carbon dioxide. The majority of the methane is released by belching by the animal, thereby contributing to green house gas increases.

Thus, there is a need for a feed supplement for animals to reduce methane and carbon dioxide production in ruminant animals.

SUMMARY OF THE EMBODIMENTS

In some embodiments, the present invention discloses a method and process to prepare sodium percarbonated feed additive polyphenol particles, including a process for preparing dry feed additive using a dispersing agent.

Feed additive polyphenol particles can be prepared by reacting phenols with sodium percarbonate ($2Na_2CO_3 \cdot 3H_2O_2$) in a solution of an organic solvent compatible with water, water, a peroxidase and a dispersing agent. For example, a process to prepare sodium percarbonated polyphenol particles can include preparing a solution of phenol in an organic solvent, water, and a peroxidase, followed by adding sodium percarbonate into the solution to obtain a reaction mixture and activating the spherical polyphenol particles.

In some embodiments, the feed additive polyphenol particles can be extracted and commercially produced by adding a dispersing agent to selectively prepare and activate polyphenol particles having desired diameters without forming micelles.

In some embodiments, polymer emulsions of activated polyphenol particles can be performed to generate secondary feed additive, which can have low viscosity for ease of mixing in feeds or diet of animals. These particles are expected to be useful in the field of feed additives used in ruminants to eliminate the formation of $CO_2$ in the environment to prevent future deterioration of the ozone layer.

BRIEF DESCRIPTION OF THE DRAWINGS

FIGS. 1A-1B illustrate flow charts for forming phenolic particles according to some embodiments.

DETAILED DESCRIPTION OF THE EMBODIMENTS

Figure 2:
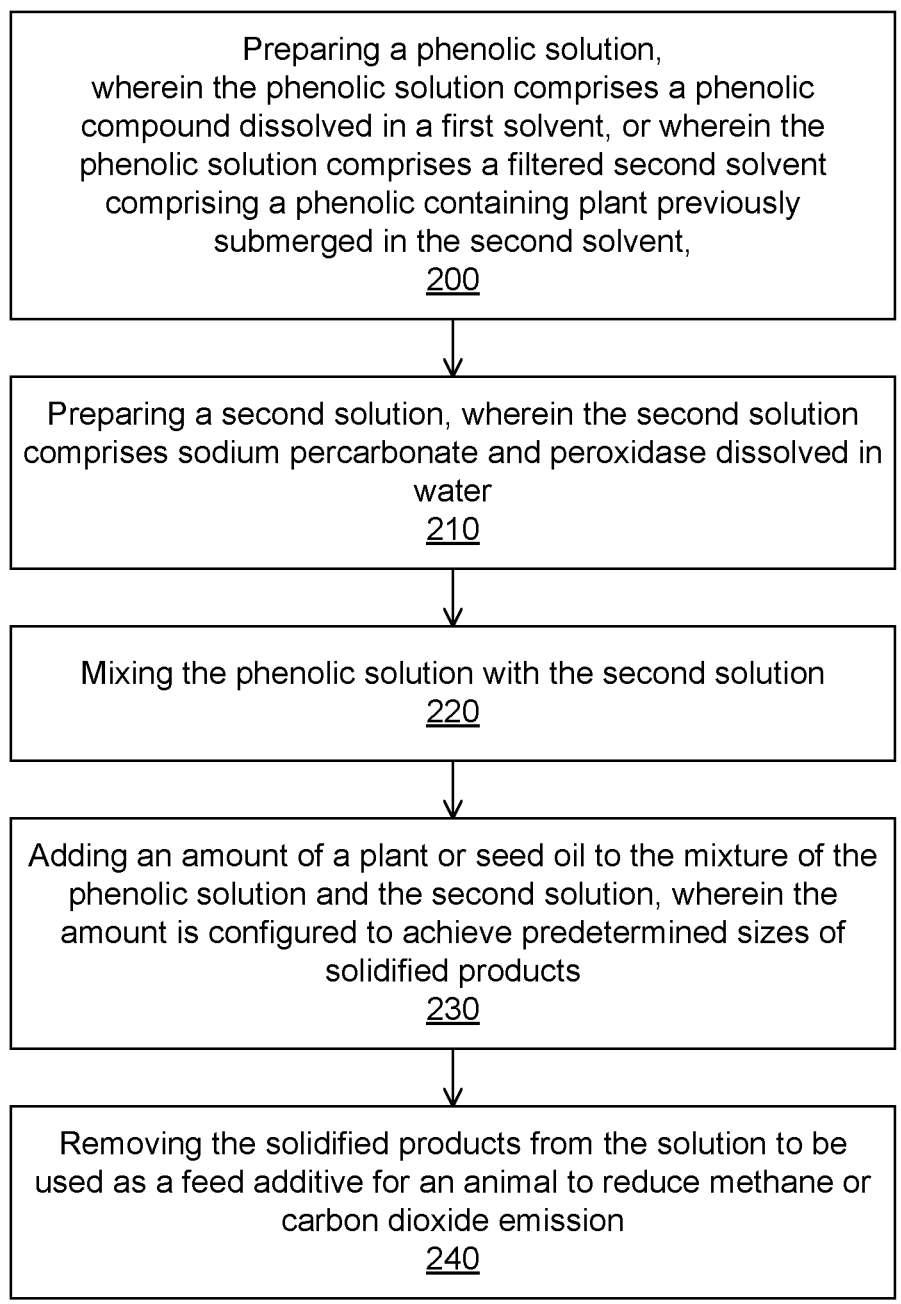
FIG. 2 illustrates a flow chart for forming a feed additive according to some embodiments.

In some embodiments, the present invention discloses an animal feed additive which can be used as a feed supplement in an animal feed. The feed additive or feed supplement can be in the form of particles or pellets that can be mixed in a regular feed diet of the animal. The feed additive can include a phenolic compound, together with sodium and carbonate components, e.g., forming sodium carbonate phenolic feed additive.

In some embodiments, the feed additive can include natural substances, such as phenolic compounds selected and activated from plant phenols, which can help reducing methane or carbon dioxide production by an animal, such as a ruminant, for example, by mixing in a feed diet of the animal. The feed diet can be optimized to enhance health, growth, meat, and milk production of the animals.

In some embodiments, the feed additive can include sodium and carbonate components, which can help in dissolving the phenolic feed additive during the consumption of the feed additive by the animal. The incorporation of the sodium and carbonate components can be accomplished by using an oxidant having sodium percarbonate, which can be dissolved in a water solution to release sodium and carbonate ions for reacting with the phenolic feed additive.

In some embodiments, the present invention discloses a method for reducing methane or carbon dioxide production in animals, such as in ruminants, which includes feeding orally to the animal a feed composition containing a sodium carbonate phenolic feed additive.

The animal feed supplement described herein can be used to reduce methane and carbon dioxide production or emission by animals, while increasing availability of nutrients, increase efficiency of milk and meat production by the animals. The present sodium carbonate phenolic feed additive has been added to beef cow diet and can reduce their methane emissions by as much as 82% to 90% percent, in addition to allow the cows to convert feed to body weight 20 percent more efficiently. Further, the efficacy of the present feed additive does not diminish among 21 cows fed 1.5 to 3 ounces of feed additive daily for 21 weeks.

In some embodiments, the sodium carbonate phenolic feed additive can include an enzyme catalyzed oxidative crosslinking of a phenolic compound, using an oxidant having a sodium percarbonate to incorporate sodium and carbonate elements to the feed additive. The sodium carbonate phenolic feed additive can be fed to an animal to reduce methane or carbon dioxide production by the animal. For example, the feed additive can be mixed with a regular feed diet of the animal, to be orally consumed by the animal.

FIGS. 1A-1B illustrate flow charts for forming phenolic particles according to some embodiments. In FIG. 1A, operation 100 prepares a solution comprising a phenolic compound, an oxidizing agent, an enzyme and a dispersing agent. The phenolic compound, the oxidizing agent, and the enzyme are configured to generate an enzyme catalyzed oxidative polymerization of the phenolic compound. The dispersing agent is configured to limit a coalescent of polymer products formed by the enzyme catalyzed oxidative polymerization of the phenolic compound to achieve predetermined sizes. Operation 110 removes the polymer products from the solution to be used as a feed additive for an animal to reduce methane or carbon dioxide emission.

In FIG. 1B, operation 130 prepares a solution comprising a phenolic compound, an oxidizing agent comprising sodium percarbonate, an enzyme comprising horseradish peroxidase, and a dispersing agent comprising a plant or seed oil. The phenolic compound, the oxidizing agent, and the enzyme are configured to generate an enzyme catalyzed oxidative polymerization of the phenolic compound to form sodium carbonate phenolic particles. The dispersing agent is configured to limit a coalescent of phenolic particles to achieve predetermined sizes. Operation 140 removes the polymer products from the solution to be used as a feed additive for an animal to reduce methane or carbon dioxide emission.

In some embodiments, the sodium carbonate phenolic feed additive and the use of the feed additive are considered to be purely non-therapeutic. However, in some embodiments, the feed additive and its usage can be therapeutic to the animals.

In some embodiments, the sodium carbonate phenolic feed additive can be used to reduce methane and carbon dioxide production in the rumen of a ruminant, and thereby reduce or eliminate associated bloat. Thus, the feed additive can help solving a significant problem in feedlot or grazing livestock production systems due to a high-grain diet or high legume forage diet in ruminants.

In some embodiments, the animal is a ruminant animal or a pseudo-ruminant animal. The ruminant refers to any hoofed animal of the suborder Ruminantia and the order Artiodactyla, characteristically digesting its food in two steps. Ruminants include cattle, sheep, goats, llamas, giraffes, bisons, buffalo, deer, elk, wildebeest, antelope, pronghorn, alpacas and yaks. The pseudo-ruminant can include horses, camels, hippopotami, rabbits, guinea pigs, and hamsters.

The amount of the animal feed supplement consumed by the animal can vary depending on the animals, such as on types of the animals, sizes of the animals, and ages of the animals. The total daily feed supplement amount can be divided and provided in portions during the day, such as two or three portions per day. Each animal can consume up to about 100 g of feed additive per day. For example, an animal can consume less than 100 g, less than 90 g, less than 80 g, less than 70 g, less than 60 g, less than 50 g, less than 40 g, less than 30 g, less than 20 g, or less than 10 g of the feed supplement per day depending on the size of the animal. As a specific example, an average cow can consume about 40 g to 85 g of feed additive per day.

Preliminary data indicates that the feed additive disclosed in the present specification can reduce methane or carbon dioxide production and emission by as much as 82% to 90% percent compared to methane or carbon dioxide production and emission if the animal feed supplement is not consumed. Further, the effect can be a long term effect with no side effect, e.g., the animals can more efficiently convert the feed having the feed additive to body weight during at least in the 21 week study time.

General Process

In some embodiments, the feed additive can include phenol particles or pellets, which can be formed by an enzyme catalyzed oxidative crosslinking of a phenol, together with by using a dispersing agent to control the size of the phenol particles. The phenol particles can further include sodium and carbonate, for example, by using sodium percarbonate as the oxidant in the process of the enzyme catalyzed oxidative crosslinking of the phenol to form the phenol particles.

In some embodiments, the process to form the feed additive can include dissolving a phenol, such as a polyphenol or a phenolic compound, in a solvent. An oxidizing agent, or an oxidant, is then added to the solution, together with an oxidoreductase as a catalyst to oxidize the polyphenol using the oxidizing agent to form phenoxy radicals to produce polymers and oligomers. The polymers and oligomers can coalesce to form polyphenol particles. The oxidant can include sodium percarbonate, which can be dissociated into sodium and carbonate ions, together with hydrogen peroxide. The sodium and carbonate ions can be incorporated in the polyphenol particles, which can assist in dissolving the polyphenol particles during the digestion of the particles. A dispersing agent is added, for example, before the particle coalescence to control the size of the particles. The oxidative reaction is configured to form phenoxy radicals to produce polymers and oligomers, with the polymers and oligomers coalesced to form the particles.

In some embodiments, the present invention discloses a method to form an animal feed additive which can reduce methane or carbon dioxide emission from the animal. The method can include an enzyme catalyzed oxidative crosslinking or polymerizing a phenol, such as a polyphenol or a phenolic compound, to form particulate feed additive. The oxidative reaction is configured to form phenoxy radicals to produce polymers and oligomers, with the polymers and oligomers coalesced to form the particles.

The method can include forming a phenolic solution having a phenol dissolved in a solvent. The phenolic solution can be formed by dissolving a phenol, e.g., a polyphenol of a phenolic compound, in a solvent, such as an organic solvent. The solvent can be a water based or a water miscible solvent, such as water.

The phenolic solution can be formed by submerging a phenol containing substance, such as a phenol containing plant, in a solution or a solvent. The phenol can be extracted from the phenol containing plant into the solvent, and the solvent can be filtered to remove the residue, such as removing the phenol containing plant that already has the phenol dissolved in the solvent. Purity and concentration of the phenol can be increased, for example, by reverse osmosis.

The method can further include mixing the phenolic solution with an oxidant, an enzyme, and a dispersing agent. The oxidant, the enzyme, and the dispersing agent can be in solid form, liquid form, or can be dissolved in one or more solutions. The oxidant can include sodium percarbonate, or can include a combination of sodium percarbonate and hydrogen peroxide. The oxidant can be configured to oxidize the phenol with the enzyme acting as a catalyst. The dispersing agent can be configured to limit sizes of particles coalescing from the oxidation of the phenol.

The method can further include removing the particles from the mixture, including drying the particles. After dried, the particles can be added to a feed composition, to be fed to the animals.

In some embodiments, the oxidant can be dissolved in a solution, such as in water, before mixing with the phenolic solution. For example, an oxidant containing sodium percarbonate can be in solid form, and can be mixed with a water based phenolic solution. The solid form sodium percarbonate can be dissolved in water, and the water solution can be mixed with the phenolic solution.

In some embodiments, the enzyme can be dissolved in a solution, such as in water, before mixing with the phenolic solution. For example, an enzyme containing horseradish peroxidase can be in solid form, and can be mixed with a water based phenolic solution. The solid form horseradish peroxidase can be dissolved in water, and the water solution can be mixed with the phenolic solution.

In some embodiments, the dispersing agent can be dissolved or mixed in a solution, such as in water, before mixing with the phenolic solution. For example, a dispersing agent containing safflower oil can be in liquid form, and can be mixed directly with the phenolic solution.

In some embodiments, the mixture of the phenolic solution with the oxidant, the enzyme, and the dispersing agent can be formed by mixing the phenolic solution directly with the oxidant or with a solution containing the oxidant. The mixture can be formed by mixing the phenolic solution directly with the enzyme or with a solution containing the enzyme. The mixture can be formed by mixing the phenolic solution directly with the dispersing agent or with a solution containing the dispersing agent.

In some embodiments, the mixture of the phenolic solution with the oxidant, the enzyme, and the dispersing agent can be formed by mixing the phenolic solution with one or more solutions containing the oxidant, the enzyme, and the dispersing agent, e.g., the phenolic solution and the solutions containing the oxidant, the enzyme, and the dispersing agent are mixed in a common container. Other mixing configurations can be used, such as forming a mixture of the oxidant or the oxidant solution, the enzyme or the enzyme solution, the dispersing agent or the dispersing agent solution, before mixing the mixture with the phenolic solution.

Another mixing configuration can include gradually adding an oxidant or an oxidant solution to a phenolic solution or to a mixture of the phenolic solution with at least one of the enzyme (or the enzyme solution) or the dispersing agent (or the dispersing agent solution). The oxidant or the oxidant solution can be added at a rate approximately equal to the rate of consumption of the oxidant.

Another mixing configuration can include gradually adding an enzyme or an enzyme solution to a phenolic solution or to a mixture of the phenolic solution with at least one of the oxidant (or the oxidant solution) or the dispersing agent (or the dispersing agent solution). The enzyme or the enzyme solution can be gradually added to prevent excess enzyme in the mixture.

Another mixing configuration can include gradually adding a dispersing agent or a dispersing agent solution to a phenolic solution or to a mixture of the phenolic solution with at least one of the oxidant (or the oxidant solution) or the enzyme (or the enzyme solution). The dispersing agent or the dispersing agent solution can be gradually added to limit a growing of particle sizes, e.g., to control the sizes of the particles, such as to stop adding the dispersing agent when the particles reach predetermined sizes.

In some embodiments, a ratio of the phenol to the dispersing agent can be between 3 to 1 and 1 to 3. A ratio of the phenol to the oxidant can be between 0.1 to 2.5 moles of oxidant per 100 grams of phenol. A ratio of the phenol to the enzyme can be between 10 mg to 5 g of enzyme per 100 grams of phenol.

In some embodiments, the phenol can include a polyphenol extracted from pomegranate, green tea, apple peel, garlic or yucca. The solvent can include an aromatic hydrocarbon, an alcohol, an organic solvent, or mixture thereof, such as ethanol, propanol, butanol, acetone, hexane, propylene glycol, aqueous ethanol, aqueous propylene glycol.

The oxidant can further include hydrogen peroxide, e.g., a solution of sodium percarbonate and hydrogen peroxide in water, with the sodium percarbonate dissolved in the water to provide sodium and carbonate ions to be incorporated to the particles. The enzyme can include an oxidoreductase, such as horseradish peroxidase or amylase. The dispersing agent can include a grain or seed oil, such as safflower oil. The dispersing agent amount can be configured to form particles having the predetermined sizes less than 10 cm, such as between 5 and 7 cm. The dispersing agent can be added to the mixture before or during the oxidation reaction generating particles to control the size of the particles. The dispersing agent can be configured to prevent micelle formations in the mixture due to a phenolic polymerization process.

The particles can be configured to be orally consumed by the animal in mixing with other feeds. The feed additive can be configured to reduce methane or carbon dioxide upon oral consumption of the feed additive by the animal. The feed additive can further include feed grains, flavorings, colorants, micronutrients, or vitamins, seaweed, bromo chloromethane, 2-Bromoethanol sulfate, ciclodextrine and asparagopsis taxiformis or asparagopsis armata.

Phenolic Compounds

In some embodiments, the phenol or phenolic compound used to form the feed additive in the enzyme catalyzed oxidative crosslinking of the phenol or phenolic compound can be those that include a hydroxyl group bonded directly to an aromatic hydrocarbon group. The simplest of the class is phenol ($C_6H_5OH$). The phenol or phenolic compound can include a polyphenol, such as a polyphenol extracted from pomegranate, green tea, apple peel, garlic or yucca. Other polyphenol can be used, such as polyphenol obtained from a variety of sources, including, for example, fruits, vegetables, legumes, nuts, seeds, tea extracts, herbs, spices, and tree barks.

In some embodiments, the feed additive polyphenol particles can be formed by an oxidative process to polymerize a phenol or phenolic compound. The oxidative process can be an enzyme catalyzed oxidative process. The enzyme catalyzed oxidative process of the phenol can be performed in a solution, such as in an organic solvent, e.g., in an organic-non aqueous or in an organic-aqueous solvent medium. The solution or solvent medium can improve the oxidative polymerization reaction, such as producing higher yields and higher molecular weight products. Further, to control the molecular weight, e.g., to prevent the formation of micelles which can form particles too large to be consumed comfortably by the animals, a dispersing agent can be added to the solution or solvent medium.

In some embodiments, the solution medium can include a phenolic solution, e.g., a solution containing a phenol or a phenolic compound. For example, a phenolic solution containing a green tea phenol can include a green tea extract dissolved in a solution. The green tea extract can be obtained from tea leaves using a solvent, such as water, alcohol or an aromatic hydrocarbon. The green tea phenol can be hot water extracted, e.g., by submerging the tea leaves in hot water. Alternatively, the polyphenol can be obtained from the alcohol extraction of tea, or by ultrafiltration or reverse osmosis of water or alcohol extract of tea.

In some embodiments, the solvent for the phenol can include aromatic hydrocarbons. Other solvents can be used, such as alcohols, organic solvents and mixtures thereof, such as ethanol, propanol, butanol, acetone, hexane, propylene glycol, aqueous ethanol, or aqueous propylene glycol.

In some embodiments, the phenol can be dissolved in an organic solvent that is water-miscible. For example, water-miscible solvents can include ethanol, methanol, dioxane, tetrahydrofuran, dimethyl formamide, methyl formate acetone, n-propanol, isopropanol, ethanol, or t-butyl alcohol. For water miscible solvents, the oxidative polymeric reaction of the phenol can occur in the solution. The solution can have between 1/100 to 1 g/ml concentration, e.g., between 1 g to 100 g of polyphenol for 100 ml solvent.

In some embodiments, the phenol can be dissolved in a water-immiscible solvent, such as hexane, trichloromethane, methyl ethyl ketone, ethyl acetate, or butanol. For water immiscible solvents, the solvent can be dispersed in the water (or vice versa) upon mixing the solvent with the water. The oxidative polymeric reaction of polyphenol can occur at the solvent/water interface. The phenol can be polymerized in the solvent, while the enzyme and peroxide stay in the water.

In some embodiments, the organic solvent is used by an amount for completely dissolving the phenol, such as greater than 30 vol % of the total polymerization volume. The organic solvent amount should not be so large, such as less than 70 vol % of the total polymerization volume, to prevent a drastically reduction of the activity of enzyme, such as the peroxidase, as biocatalyst.

In some embodiments, the phenolic solution containing a phenol, such as a green tea phenol, can be formed directly from the phenolic containing plant, such as the tea leaves, instead of from the green tea extract. For example, the phenolic containing plant, such as the tea leaves, can be disposed in a solvent, such as water, alcohol or an aromatic hydrocarbon. To form a water solution, the plant containing the phenol, such as the tea leaves, can be submerged in hot water. The plant phenol can then be extracted from the phenolic containing plant, e.g., the plant phenol can be released from the plant into the hot water to form a water solution containing phenol. To form an alcohol solution, the plant containing the phenol, such as the tea leaves, can be submerged in alcohol. The plant phenol can then be extracted from the phenolic containing plant, e.g., the plant phenol can be released from the plant into the alcohol to form an alcoholic solution containing plant phenol For example, to form a phenolic solution from green tea, a solvent can be added to tea leaves, followed by stirring the solution. The residue can then be separated from the solution, such as by filtering. The solvent can be heated, for example, to a temperature slightly less than the boiling temperature of the solvent to reduce the phenol extraction time. The stirring time can be based on the solvent temperature, such as between 10 minutes in hot solvents to several hours in room temperature solvents. Improving concentration of the phenol extract in the solution can be obtained by filtering or by reverse osmosis.

Oxidizing Agent

In some embodiments, the feed additive can be formed by an enzyme catalyzed oxidative crosslinking or polymerizing a phenol or a phenolic compound. The oxidative process can include an oxidizing agent or an oxidant, e.g., a reactive oxygen species.

The oxidizing agent or the oxidant can include a peroxide or a peroxide releasing compound, such as sodium percarbonate. The usage of sodium percarbonate can provide an additional benefit of helping to dissolve the particles during the digestion of the feed having the feed additive particles.

In some embodiments, the feed additive can be modified to add other additives which are beneficial to the digestion and health of the animal. For example, the feed additive can be modified to include useful chemicals such as sodium and carbonate, which can help with the digestion of the feed. This modification can be made by using an oxidizing agent or an oxidant having a carbonate salt such as sodium percarbonate. Sodium percarbonate can release hydrogen peroxide, which can also be used as a source of oxidizing agent. For example, sodium percarbonate can be dissolved in water to release hydrogen peroxide.

The process to form the feed additive can include an oxidizing agent having a sodium percarbonate dissolved in water. The sodium percarbonate component can provide the oxidative property by the hydrogen peroxide generated by the sodium percarbonate dissociated in water. The sodium percarbonate component can provide sodium and carbonate ions, generated by the sodium percarbonate dissociated in water, to be incorporated to the feed additive for easy of dissolving the feed additive when digested by the animal.

In some embodiments, the oxidizing agent or the oxidant can include a combination of a peroxide and a peroxide releasing compound. For example, the oxidizing agent can include a solution of sodium percarbonate and hydrogen peroxide. The amount of sodium percarbonate in the oxidizing agent can be determined to optimize the amount of sodium and carbonate in the feed additive. The amount of hydrogen peroxide in the oxidizing agent can be determined to supplement the hydrogen peroxide released from the sodium percarbonate in the oxidative process of the phenol, e.g., the combination of the sodium percarbonate release hydrogen peroxide and the hydrogen peroxide directly added to the oxidizing agent is suitable for the oxidative polymerization process of the phenol in the solution.

In general, the oxidizing agent or oxidant can include reactive oxygen species, which can facilitate the oxidation of a phenolic compound to form a reactive quinone structure upon a bioactivation. For example, the reactive oxygen species can be hydrogen peroxide, superoxide anion, singlet oxygen, or a hydroxyl radical. In some embodiments, the oxidizing agent can include methyl peroxide, ethyl peroxide, hydroalkyl peroxide, t-butylhydroperoxide, or ethylhydroperoxide. In some embodiments, the oxidizing agent can include a material that release hydrogen peroxide such as hydration of adducts of hydrogen peroxide, including carbamide peroxide, magnesium peroxide, and sodium percarbonate. In some embodiments, the oxidizing agent can include a combination of different reactive oxygen species, such as hydrogen peroxide and sodium percarbonate.

The oxidizing agent can be used in an amount of about 0.1 to 2.5 moles per 100 grams polyphenol, or about 0.1 to 0.5 moles per 100 grams polyphenol. For example, the oxidizing agent of hydrogen peroxide can be dissolved in water with a concentration from about 1 mM to 10 M, or about 0.1% to about 10% hydrogen peroxide solution.

In some embodiments, the process to form the feed additive can utilize sodium percarbonate as the oxidizing agent. For example, sodium percarbonate can be added to a water solution. Sodium percarbonate can dissolve in the water solution to give $Na^+$, $CO_3^{2-}$, and $H_2O_2$. In some embodiments, sodium percarbonate can be added to the phenolic solution, e.g., the solution having the phenolic compound dissolved in a solvent or the water based solvent having the phenolic compound dissolved therein. Since the phenolic solution includes water, sodium percarbonate can be dissolved to provide sodium and carbonate ions to be incorporated to the phenolic feed additive product, together with hydrogen peroxide to function as the oxidizing agent.

Enzyme Component

In some embodiments, the feed additive can be formed by an enzyme catalyzed oxidative crosslinking or polymerizing a phenol or a phenolic compound. The oxidative process of the phenol can be performed in a solution including phenol, an oxidizing agent, and an enzyme, with the enzyme functioned as a catalyst for the oxidative process. The enzyme can include an oxidoreductase, such as a peroxidase, which can be a catalyst for an oxidizing agent of hydrogen peroxide.

In some embodiments, the solution can include a mixture of a phenol solution, a solution having the oxidizing agent, and a solution having the enzyme. For example, the phenol solution can include a plant containing phenol disposed in a solvent. Alternatively, the phenol solution can include a phenol extract dissolved in an organic solvent. The solution having the oxidizing agent can include a solution of hydrogen peroxide, e.g., an amount of hydrogen peroxide in water, or a water-diluted amount of hydrogen peroxide. The solution having the oxidizing agent can include a solution of sodium percarbonate, e.g., an amount of sodium percarbonate dissolved in water. The solution having the oxidizing agent can include a solution of hydrogen peroxide and sodium percarbonate, e.g., a water solution having an amount of hydrogen peroxide and an amount of sodium percarbonate dissolved therein.

In some embodiments, a phenolic solution can be prepared, for example, by dissolving a phenol extract in a solvent, or by submerging a phenol containing component, such as a phenol containing plant, in a solvent to extract the phenol from the phenol containing plant into the solvent. The solvent containing the phenol containing plant can be filtered, purified, and adjusting a concentration suitable for the oxidative process. For example, the concentration of the phenol in the solvent can be reduced by adding additional solvent. The concentration of the phenol in the solvent can be increased by a reverse osmosis process.

An oxidizing agent can be added to the phenolic solution, such as adding sodium percarbonate in a powder form, or a solution containing sodium percarbonate. An enzyme, such as a peroxidase, can be also added to the phenolic solution, which can function as a catalyst for the oxidation of the polyphenol using the peroxide released by the sodium percarbonate. The enzyme can be added to the phenolic solution in the form of a solution containing the enzyme, or the enzyme can be directly added to the phenolic solution.

The oxidizing agent and the enzyme can be added to the phenolic solution in any order, such as the oxidizing agent (or the solution containing the oxidizing agent) is added to the phenolic solution, followed by adding the enzyme (or the enzyme solution). Alternatively, the enzyme (or the enzyme solution) is added to the phenolic solution, followed by adding the oxidizing agent (or the solution containing the oxidizing agent).

The peroxidase enzyme can catalyze, with hydrogen peroxide, the oxidation of a variety of phenols. The peroxidase enzyme can include horseradish peroxidase. Phenolic free radicals can be generated, which diffuse from the active center of the enzyme into the solution. The phenolic free radicals then can polymerize to polyaromatic products. The polyaromatic products are high molecular weight polymers and are water-insoluble, e.g., forming phenol particles. The phenol particles can be separated by filtration from water.

In some embodiments, the enzyme can function to oxidize the phenols, such as by catalyzing redox reactions, i.e., the transfer of electrons from the phenolic compound to molecular oxygen. The phenol oxidizing enzyme can include peroxidases, which are an oxidoreductase class of enzymes, which catalyze oxidoreduction reactions. The peroxidase enzyme catalyzes the decomposition of hydrogen peroxide into water and molecular oxygen.

The phenol oxidizing enzyme can also include polyphenol oxidase, monophenol oxidase, oxidases forming hydrogen peroxide and peroxidases. The phenol oxidizing enzyme can include oxidoreductases such as oxidoreductases that act on the CH—OH group of donors (e.g., alcohol oxidoreductases), oxidoreductases that act on the CH—OH group of donors (e.g., alcohol oxidoreductases), oxidoreductases that act on diphenols and related substances as donors (e.g., catechol oxidase), or oxidoreductases that act on peroxide as an acceptor (e.g., peroxidases, such as horseradish peroxidase or amylase). Other oxidoreductases or peroxidases can be used, such as soybean peroxidase, Coprinus peroxidase or *Aspergillus*, chloroperoxidase and other haloperoxidases, lactoperoxidase, bacterial peroxidases, fungul laccase and tyrosinase.

In some embodiments, the enzyme, such as horseradish peroxidase, can be dissolved in water and added to the phenolic solution. The concentration of the enzyme solution can be in a wide range, such as about 10 milligrams to 5 grams for each 100 grams of polyphenol or about 10 to 365 mg per liter. The enzyme functions as a catalyst which is not consumed in the reaction, and can be recovered after the reaction.

Dispersing Agent

In some embodiments, the phenol particles formed by an oxidative process can be controlled to achieve predetermined sizes, for example, by using a dispersing agent in the solution medium to control the molecular weight of the polymer products in the oxidative process. A dispersing agent is a substance that can improve the separation of particles in a suspension medium. The dispersing agent is different from a surfactant, which is a substance that can lower the surface tension between two phases of matter. In the solution medium of the oxidative process, the dispersing agent can be a substance that can allow disruption and dispersion to disturb the phenolic polymerization, such as to prevent the formation of micelles and to form pellets. Depending on the amount of the dispersing agent in the oxidative solution medium, the pellet sizes can be controlled. For example, a large amount of dispersing agent in the solution medium can greatly disrupt and disperse the phenolic polymerization, which can result in small size of the polymerized particle pellets.

A dispersing agent, such as a grain or seed oil, such as safflower oil, can be used to prevent the formation of micelles during the polymerization process. For example, an amount of oil can be mixed in a solution of phenol, oxidizing agent and enzyme to control the sizes of the phenol particles. A large amount of oil added to the solution can significantly disperse the polymers and oligomers resulted from the oxidative polymerization process, resulting in smaller particles. Other dispersing agent can be used, such as Polyvinyl alcohol (PVA), Soy Lecithin or sodium dodecyl sulfate (SDS).

In some embodiments, the oxidative process can include reacting a phenol in a solution with an oxidizing agent in the presence of an enzyme functioned as an oxidation catalyst. A dispersing agent can be added to the solution, which can function to optimize the sizes of the oxidized phenol particles. For example, a dispersing agent of a grain or seed oil can be added to a mixture of a phenolic solution and a solution containing an oxidizing agent and enzyme to control the size of the particles coalesced by the polymers and oligomers resulting from the oxidative polymerization of the phenol. The particles can include sodium and carbonate, generated from an oxidizing agent containing sodium percarbonate, which can result in sodium carbonate feed additive polyphenol particles, which can be removed from the solution to be dried.

In some embodiments, the feed additive can be formed by an enzyme catalyzed oxidative crosslinking or polymerizing a phenol or a phenolic compound. The oxidative process of the phenol can be performed in a solution including phenol, an oxidizing agent, an enzyme, and a dispersing agent, with the dispersing agent functioned to control the molecular weight and the form factors of the products, such as to reduce and eliminate the formation of micelles and promote the formation of pellets. The sizes of the particles can be chosen to be easily consumed by the animals, such as having a comparable size with the other feeds. In some embodiments, a dimension of the particles can be less than 10 cm, between 3 and 9 cm, such as between 5 and 7 cm.

In some embodiments, the solution can include a mixture of a phenol solution, an oxidizing agent or a solution having the oxidizing agent, an enzyme or a solution having the enzyme, and a dispersing agent or a solution having the dispersing agent. The oxidizing agent, the enzyme, and the dispersing agent can be provided in one or more solutions.

In some embodiments, a solution or solvent medium can be produced by preparing separate one or more solutions for the phenol, the oxidizing agent-containing element, the enzyme, and the dispersing agent, followed by mixing the separate solutions. For example, the phenol can be dissolved in an organic solvent. The oxidizing agent-containing element, enzyme and dispersant can be dissolved in water. The organic solvent solution containing the phenol and the water solution containing oxidizing agent-containing element, enzyme and dispersant can be gradually added to a common reaction vessel.

In some embodiments, the solution having the oxidizing agent, the solution having the enzyme, and the solution having the dispersing agent can be three separate solutions. For example, an oxidizing agent of sodium percarbonate can be used, and can be dissolved in water to form the solution having the oxidizing agent. An enzyme of horseradish peroxidase can be used, and can be dissolved in water to form the solution having the enzyme. A dispersing agent of safflower oil can be used, and can be emulsified in water to form the solution having the dispersing agent. The three water solutions can be mixed together with the phenol solution to generate the enzyme catalyzed oxidative polymerization of the phenol.

In some embodiments, the solution having the oxidizing agent and the solution having the enzyme can be two separate solutions, with the dispersing agent added to either one of the two solutions. For example, sodium percarbonate can be dissolved in water to form the solution having hydrogen peroxide oxidizing agent (together with and sodium and carbonate ions). Horseradish peroxidase can be dissolved in water to form the solution having the enzyme of horseradish peroxidase. Safflower oil can be added to the solution having the hydrogen peroxide oxidizing agent or to the solution having the horseradish peroxidase enzyme. The two water solutions can be mixed together with the phenol solution to generate the enzyme catalyzed oxidative polymerization of the phenol.

In some embodiments, the solution having the oxidizing agent, the solution having the enzyme, and the solution having the dispersing agent can be a single solution having the oxidizing agent, the enzyme, and the dispersing agent. For example, sodium percarbonate can be dissolved in water to form the solution having hydrogen peroxide oxidizing agent (together with and sodium and carbonate ions). Horseradish peroxidase and safflower oil can be added to the solution having the hydrogen peroxide oxidizing agent. The water solution can be mixed with the phenol solution to generate the enzyme catalyzed oxidative polymerization of the phenol.

Alternatively, horseradish peroxidase can be dissolved in water to form the solution having the horseradish peroxidase enzyme. Sodium percarbonate and safflower oil can be added to the solution having the horseradish peroxidase enzyme. The water solution then can be mixed with the phenol solution to generate the enzyme catalyzed oxidative polymerization of the phenol.

In some embodiments, a phenolic solution can be prepared. An oxidizing agent can be added to the phenolic solution, such as adding sodium percarbonate in a powder form, or adding a solution containing sodium percarbonate. An enzyme can be also added to the phenolic solution, such as adding horseradish peroxidase in a powder form, or adding a solution containing horseradish peroxidase. A dispersing agent can be added to the phenolic solution, such as adding safflower oil. The oxidizing agent, the enzyme, and the dispersing agent can be added to the phenolic solution in any order. Alternatively, some of the oxidizing agent, the enzyme, and the dispersing agent can be mixed together first before adding the mixture to the phenolic solution.

In some embodiments, the phenolic solution can be added to a mixture of one or more solutions of the oxidizing agent, the enzyme, and the dispersing agent. The molecular weight of the phenolic products can be adjusted through the use of a dispersant. For example, the phenolic products can be used as food additive particles or pellets, which can be added to feeds or diet of an animal. In some embodiments, the particle size can be between 5.7 cm and 6.35 cm.

In some embodiments, the organic solvent solution containing the phenol and the water solution containing enzyme and dispersant are mixed first, and the peroxide-containing element, such as the sodium percarbonate powder or the sodium percarbonate solution, is gradually added. The amount of sodium percarbonate can be added at a controlled rate which is approximately equal to the rate at which it is consumed, since excess peroxide can inhibit the polymerization of phenol.

In some embodiments, the organic solvent solution containing the phenol and the water solution containing enzyme and dispersant are mixed first. Oxygen or peroxide can be added if the enzyme is an oxidase enzyme or a peroxidase enzyme, respectively. The phenol can react with the oxidizing agent (e.g., oxygen or peroxide) under the enzyme catalyst to generate phenolic radicals, which can react together to form the phenol particles.

In some embodiments, the volume ratio of organic solvent and water can be between 1:25 and 25:1, e.g., between 1 volume part of solvent for 25 volume part of water and 25 volume part of solvent for 1 volume part of water. The volume ratio of organic solvent and water can be between 1:5 and 5:1, e.g., between 1 volume part of solvent for 5 volume part of water and 5 volume part of solvent for 1 volume part of water. The volume ratio of organic solvent and water can be between about 1:1, e.g., about 1 volume part of solvent for 1 volume part of water.

Temperature and pH

In some embodiments, the reaction of the polyphenol can be performed at a temperature between about 0° to 40° C., since certain enzymes can be temperature sensitive and lose their activity at too high temperatures. For example, horseradish peroxidase can be inactive at temperatures above about 60° C.

In some embodiments, the reaction of the polyphenol can be performed at a pH in the range of 4 to 12, or between 4 and 9. A pH can be selected at which the enzyme is highly active. For example, an active pH value for a peroxidase can be about 6.

Oxidative Process

Phenol oxidation in plant systems can generate oxidized-polyphenol, or quinonic compounds, with multiple quinonic groups that are capable of covalent bonding. Once formed, the oxidized-polyphenol can spontaneously form covalent intra- and inter-chain crosslink to polymerize the polyphenol to form polyphenol particles.

In some embodiments, the process of forming polyphenol particles can include selecting the polyphenol, selecting the solvent for the polyphenol, selecting the oxidant-containing additive, selecting the enzyme, selecting the dispersant, and determining the ratios of the selected components. The components can be mixed to obtain polyphenol particles having embedded additive. The polyphenol particles can be removed from the solution to be dried. The dried polyphenol particles can be used as feed additive for animal. The polyphenol particles can be modified by adding sodium percarbonate, for example, by mixing the phenol reaction with sodium percarbonate.

For example, the process can include a mixture of a solvent containing phenolic compound in a desired ratio with sodium percarbonate dissolved in water. Horseradish peroxidase enzyme can be added to act as a catalyst for the hydrogen peroxide released from the dissolved sodium percarbonate. Grain or seed oil, such as safflower oil, can be added as dispersant. The phenolic compounds can include a mixture of a pomegranate extract and a green tea extract. The ratio of phenolic compound to sodium percarbonate can range from about 1:2 to about 1:20 on a wt/wt basis (molar weight), or from about 3:1 to about 1:3 on a wt/wt basis (molar weight).

As an example, 30 mg of horseradish peroxidase, 1.5 g of phenylphenol dissolved in 40 ml of ethanol, 10 g of a dispersant, and 12 ml of 3% hydrogen peroxide are added drop-wise to a constantly-stirred container. After 10 minutes, the product was collected by filtration. The product is then air dried. As another example, 300 mg of horseradish peroxidase dissolved in 100 ml of water, 8.3 g of phenylphenol dissolved in 200 ml of ethanol, 10 g of sodium percarbonate dissolved in 100 ml of water, 10 g of a dispersant are added drop-wise to a constantly-stirred container. After 15 minutes, the product was collected by filtration. The product is then air dried.

In some embodiments, the present invention discloses a method to form an animal feed additive which can reduce methane or carbon dioxide emission from the animal. The method can include forming a phenolic solution having a phenol dissolved in a solvent. The phenolic solution can be formed by dissolving a phenol, e.g., a polyphenol of a phenolic compound, in a solvent, such as an organic solvent. The phenolic solution can be formed by submerging a phenol containing substance, such as a phenol containing plant, in a solution or a solvent, to extract the phenol into the solvent. The solvent can be a water based solvent or water miscible solvent.

The method can further include mixing the phenolic solution with an oxidant or a solution containing an oxidant, such as sodium percarbonate. The method can further include mixing the phenolic solution with an enzyme or a solution containing an enzyme, such as a peroxidase. The peroxidase can function as a catalyst in an oxidation reaction between the oxidant and the phenol. The method can further include mixing the phenolic solution with a dispersing agent or a solution containing a dispersing agent, such as a grain or seed oil. The dispersing agent can be added an amount configured to achieve predetermined sizes of particles coalescing from the oxidation reaction. The sodium percarbonate can be configured to incorporate sodium and carbonate to the particles with amounts at least sufficient to assist in dissolving the particles when the animal digests the particles.

The method can further include removing the particles from the mixture, including drying the particles. After dried, the particles can be added to a feed composition, to be fed to the animals.

In some embodiments, the oxidant can include a mixture of sodium percarbonate and hydrogen peroxide. The amount of sodium percarbonate is configured to provide adequate sodium and carbonate to be incorporated in the particles. And the addition of hydrogen peroxide to provide enough oxidant to the oxidative process.

FIG. 2 illustrates a flow chart for forming a feed additive according to some embodiments. Operation 200 prepares a phenolic solution. The phenolic solution can include a phenolic compound dissolved in a first solvent. Alternatively, the phenolic solution can include a filtered second solvent comprising a phenolic containing plant previously submerged in the second solvent. Operation 210 prepares a second solution, with the second solution having sodium percarbonate and peroxidase dissolved in water. Operation 220 mixes the phenolic solution with the second solution. Operation 230 adds an amount of a plant or seed oil to the mixture of the phenolic solution and the second solution, the amount configured to achieve predetermined sizes of solidified products. Operation 240 removes the solidified products from the solution to be used as a feed additive for an animal to reduce methane or carbon dioxide emission.

Figure 3:
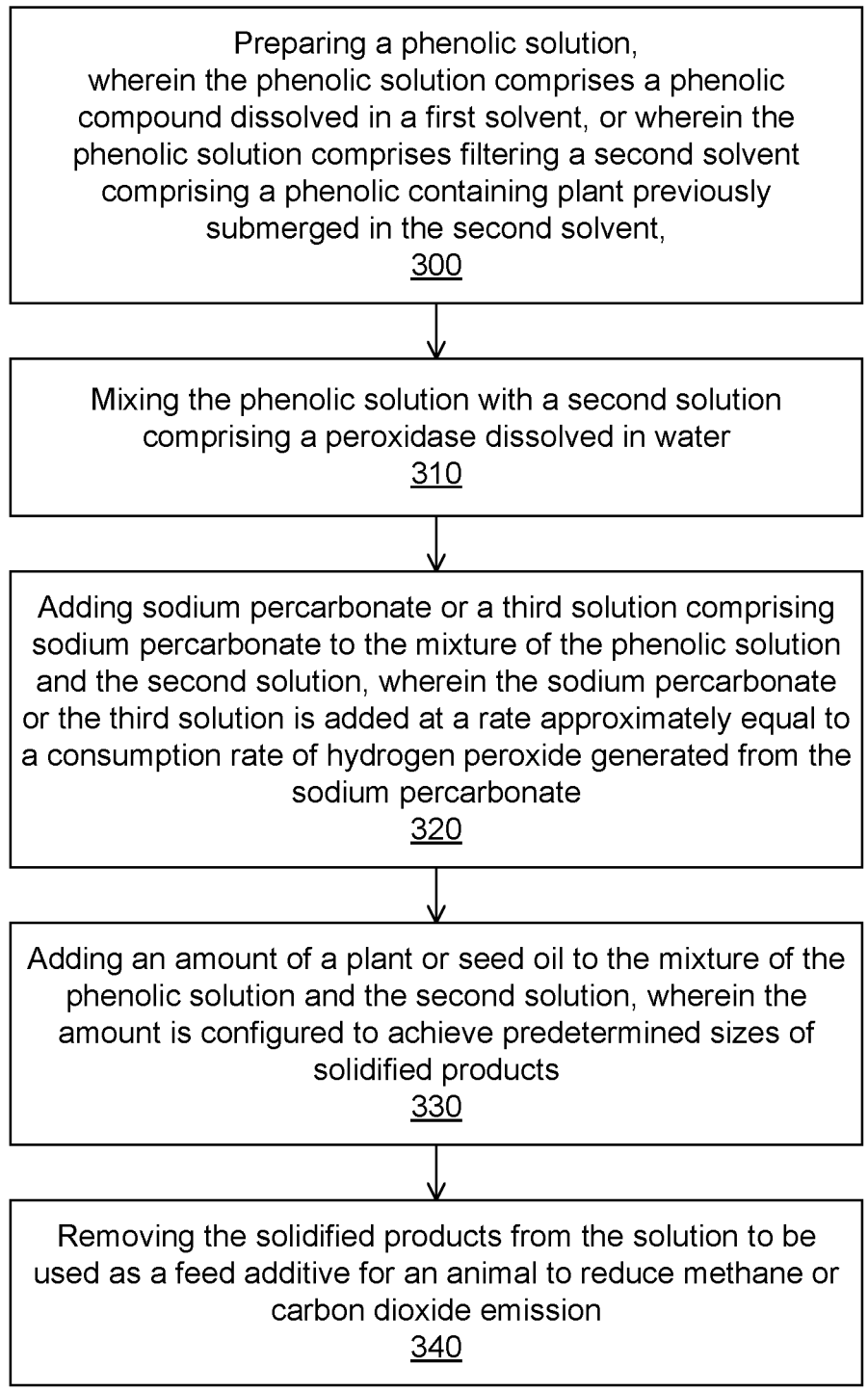
FIG. 3 illustrates a flow chart for forming a feed additive according to some embodiments.

FIG. 3 illustrates a flow chart for forming a feed additive according to some embodiments. Operation 300 prepares a phenolic solution. The phenolic solution can include a phenolic compound dissolved in a first solvent. Alternatively, the phenolic solution can include a filtered second solvent comprising a phenolic containing plant previously submerged in the second solvent. Operation 310 mixes the phenolic solution with a second solution having a peroxidase dissolved in water. Operation 320 adds sodium percarbonate or a third solution having sodium percarbonate to the mixture of the phenolic solution and the second solution. The sodium percarbonate or the third solution is added at a rate approximately equal to a consumption rate of hydrogen peroxide generated from the sodium percarbonate. Operation 330 adds an amount of a plant or seed oil to the mixture of the phenolic solution and the second solution. The amount is configured to achieve predetermined sizes of solidified products. Operation 340 removes the solidified products from the solution to be used as a feed additive for an animal to reduce methane or carbon dioxide emission.

Feed Supplement

In some embodiments, the phenolic products can be used as a feed additive, since phenolic compounds can be beneficial as potential feed additives for animals, especially in term of methane and carbon dioxide reduction. The feed additive can be combined with an animal feed to form an animal feed composition. The phenolic additive can reduce methane and carbon dioxide emissions by animals, such as ruminant animals.

The animal feed additive can be added to the feed grains or diet to the animals, such as cows, in the form of animal feed. The animal feed additive can include other components in addition to the active materials, such as, for example, flavorings, colorants, micronutrients, and vitamins. The animal feed additive can include substances to reduce $CO_2$ production, such as Bromo Chloromethane, 2-Bromoethanol sulfate, ciclodextrine and asparagopsis taxiformis or asparagopsis armata.

Feed is given to domestic animals to provide nutritive substances to the animals. The feed additive can be added to feed at the time of feeding to the animals. Alternatively, the feed additive can be added to feed at the time of feed formulation, e.g., the feed additive can be formulated along with feed components. In general, the animal feed additive is not sufficient on its own to meet the nutritional need of the animal.

The feed additive can be prepared in the dry solid form, for example, pellet form, which is suitable for addition to animal feed in order to provide beneficial effects, including reducing methane and carbon dioxide emissions by the animals. The feed additive can be subject to further processing steps depending on the types of the formulation for the intended finished products, including molded, pressed, spray dried or formed into a shape with dimensions or textures suitable for consumption by the animals.

The feed additive can be used to be added on top an animal feed ration or can be used to blend into a total mixed ration. For example, the feed additive can be combined with an animal feed to form an animal feed composition.

In some embodiments, the feed additive can be consumed by the animals together with their usual animal feed. Alternatively, the feed additive can also be consumed by the animal separately to any animal feed.

In some embodiments, the polyphenol particles can be used to prepare a secondary feed additive by polymer emulsions having low viscosity for improvement of work efficiency, which can facilitate the mixing with normal feed.

What is claimed is:

1. A method of forming particles for an animal feed additive for reducing carbon dioxide emission from the animal, the method comprising
    forming a first solution comprising a phenol dissolved in a solvent;
        wherein the phenol comprises a polyphenol extracted from pomegranate, apple peel, garlic or yucca,
        wherein the solvent comprises an aromatic hydrocarbon,
    mixing the first solution with a second solution comprising an oxidant, an enzyme, and a dispersing agent,
        wherein the enzyme comprises horse radish peroxidase or amylase,
        wherein the oxidant comprises sodium percarbonate,
        wherein the oxidant is configured to oxidize the phenol with the enzyme acting as a catalyst,
        wherein the dispersing agent is configured to limit sizes of particles coalescing from the oxidation of the phenol;
        wherein the dispersing agent comprises a grain or seed oil, and
    removing the particles from the mixture.

2. A method as in claim 1,
    wherein the mixture is formed by gradually adding the second solution, wherein the second solution is added at a rate which is approximately equal to the rate of consumption of the oxidant.

3. A method as in claim 1,
    wherein a ratio of the phenol to the dispersing agent is between 3 to 1 and 1 to 3,
    wherein a ratio of the phenol to the oxidant is between 0.1 to 2.5 moles of oxidant per 100 grams of phenol, and
    wherein a ratio of the phenol to the enzyme is between 10 mg to 5 g of enzyme per 100 grams of phenol.

4. A method as in claim 1, further comprising
    adding seaweed, bromo chloromethane, 2-Bromoethanol sulfate, ciclodextrine and asparagopsis taxiformis or asparagopsis armata to the mixture.

5. A method as in claim 1,
    wherein the dispersing agent amount is configured to form particles having a predetermined size between 5 and 7 cm.

6. A method as in claim 1,
    wherein the feed additive further comprises feed grains, flavorings, colorants, micronutrients, or vitamins,
    wherein the feed additive further comprises seaweed, bromo chloromethane, 2-Bromoethanol sulfate, ciclodextrine and asparagopsis taxiformis or asparagopsis armata,
    wherein the feed additive is configured to reduce carbon dioxide upon oral consumption of the feed additive by the animal.

* * * * *